United States Patent [19]

Sheu

[11] Patent Number: 5,692,495
[45] Date of Patent: Dec. 2, 1997

[54] METHOD AND APPARATUS FOR THE PRODUCTION OF NITRIC OXIDE GAS MIXTURE

[75] Inventor: Lien-Lung Sheu, Scotch Plains, N.J.

[73] Assignee: The BOC Group, Inc., New Providence, N.J.

[21] Appl. No.: 626,413

[22] Filed: Apr. 2, 1996

[51] Int. Cl.$^6$ .......................... A61M 15/00; C01B 21/26
[52] U.S. Cl. ........................... 128/203.12; 423/403
[58] Field of Search ...................... 95/56, 153, 154; 423/403; 128/203.12

[56] References Cited

U.S. PATENT DOCUMENTS

| | | | |
|---|---|---|---|
| 2,647,822 | 8/1953 | Pike | 423/403 |
| 3,660,024 | 5/1972 | Gillespie | 423/403 |
| 3,873,675 | 3/1975 | Roters | 423/403 |
| 4,774,069 | 9/1988 | Handley | 423/403 |
| 4,869,891 | 9/1989 | Handley . | |
| 5,396,882 | 3/1995 | Zapol . | |
| 5,417,950 | 5/1995 | Sheu et al. . | |
| 5,558,083 | 9/1996 | Bathe et al. | 128/203.12 |

OTHER PUBLICATIONS

Catalysts for Oxidation of Ammonia to Oxides of Nitrogen, S.L. Handforth and J.N. Tilley, Eastern Laboratory of El du Pont de Nemours & Company, Inc., Gibbstown, NJ –Industrial Engineering and Chemistry vol. 26, No. 12 Sep. 1934, pp. 1288–1292.

Kinetics of NH3 Oxidation of Pt, Rh, and Pd, T. Pignet and L.D. Schmidt, Journal of Catalysis 40, pp. 212–225 (1975).

A New Research Pilot Plant Unit for Ammonia Oxidation Processes and Some Gauze Data Comparisons for Nitric Acid Process, Ronald M. Heck, John C. Bonacci, W. Robert Hatfield, and Thomas H. Hsiung, Ind. Eng. Chem Process Des. Devl. vol. 21, No. 1, 1982 pp. 73–79.

*Primary Examiner*—Vincent Millin
*Assistant Examiner*—Robert N. Wieland
*Attorney, Agent, or Firm*—Coleman R. Reap; Salvatore P. Pace

[57] ABSTRACT

A therapeutic oxygen-nitric oxide gas mixture is produced by passing air, oxygen-enriched air or air containing a small amount of ammonia over a noble metal catalyst at an elevated temperature. The product gas containing nitric oxide and a small amount of nitrogen dioxide is passed through a bed of an adsorbent which preferentially adsorbs nitrogen dioxide to produce nitric oxide-containing air suitable for administering to humans as an inhalant.

15 Claims, 1 Drawing Sheet

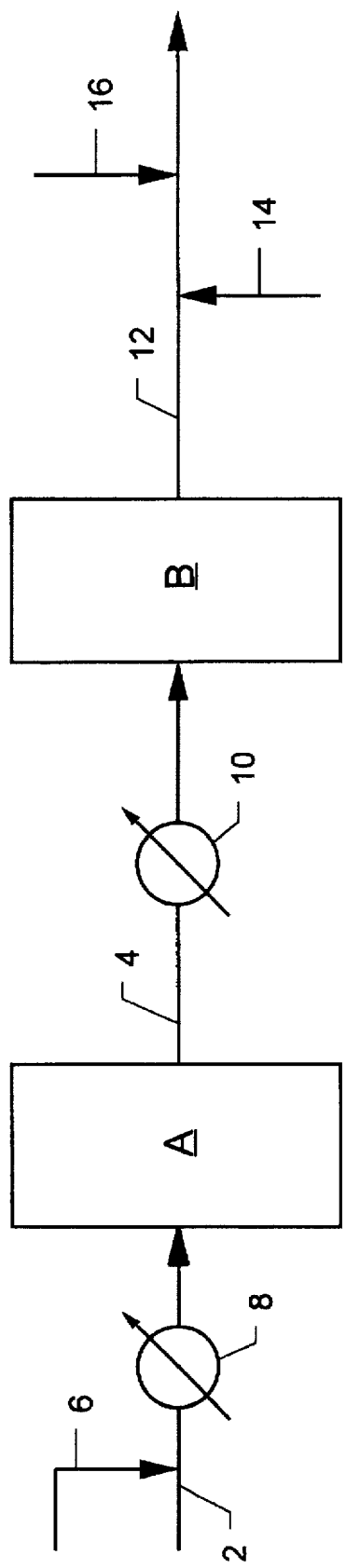

METHOD AND APPARATUS FOR THE PRODUCTION OF NITRIC OXIDE GAS MIXTURE

FIELD OF THE INVENTION

This invention relates to the production of nitric oxide gas mixtures and more particularly to the production of nitric oxide-oxygen-nitrogen gas mixtures that are suitable for use in medical applications.

BACKGROUND OF THE INVENTION

Nitric oxide has recently been found to play an important role in life processes in humans and animals. For example, it helps maintain blood pressure by dilating blood vessels, and kills foreign invaders in the body's immune system. Studies indicate that extraordinary benefits may be obtained by administering small dosages of nitric oxide to patients who suffer from certain illnesses or diseases. Of particular interest is the prospect of reducing pulmonary vasoconstriction in pediatric patients with congenital heart disease complicated by pulmonary artery hypertension by having the patients inhale oxygen-enriched air containing very small concentrations of nitric oxide.

Nitric oxide is a relatively stable gas when it is in the pure state or mixed with an inert gas, such as nitrogen or argon. However when it is mixed with oxygen it reacts rapidly with the oxygen to form nitrogen dioxide, a substance that is highly toxic to humans. The nitrogen dioxide reacts with water to form nitric and nitrous acids, which, when inhaled can cause severe pulmonary oedema, acid pneumonitis or even death. Because of the highly toxic character of nitrogen dioxide, nitric oxide that is intended for inhalation use by humans is generally purified to remove any nitrogen dioxide that is initially in the nitric oxide product as a result of the manufacturing process, and the purified product is stored and shipped in an oxygen-free environment to prevent the subsequent generation of nitrogen dioxide in the storage or shipping container.

Nitric oxide is generally administered to a patient by diluting a nitrogen-nitric oxide concentrate gas containing about 1000 ppm nitric oxide with oxygen or oxygen-enriched air carrier gas to produce an inhalation gas containing nitric oxide in the desired concentration range (usually about 0.5 to 200 ppm, based on the total volume of the inhalation gas). The concentrate is generally provided in large cylinders which are cumbersome and inconvenient for a patient to use in his home or while he is traveling.

U.S. Pat. No. 5,396,882 discloses a device for the generation of nitric oxide by subjecting a stream of air to an electric arc discharge. This method involves the use of complex and expensive equipment and produces the nitric oxide on an intermittent basis. Furthermore, the electric discharge also results in the production of ozone, which must be removed from the gas mixture prior to administering the gas to the patient.

The present invention provides apparatus and a method of producing a continuous stream of a gaseous mixture of nitric oxide without producing ozone as a byproduct.

SUMMARY OF THE INVENTION

In accordance with the invention, a continuous stream of nitric oxide-containing gas which is suitable for use as an inhalant by medical patients is generated at the site at which it is to be used. In a broad embodiment of the invention, the nitric oxide-containing gas is produced by contacting a mixed stream comprising oxygen and nitrogen or oxygen and ammonia or oxygen, nitrogen and ammonia through a bed of catalyst at a temperatures of at least 300° C. and up to about 1200° C., the catalyst being effective to cause reaction between the oxygen and one or both of nitrogen and ammonia to produce nitric oxide. The gaseous product exiting the catalyst bed is subjected to a purification step to remove nitrogen dioxide therefrom. The process is preferably carried out on a substantially continuous basis to produce a substantially continuous stream of nitric oxide-containing gas which contains a substantially constant concentration of nitric oxide and which is substantially free of nitrogen dioxide.

The nitric oxide synthesis reaction is preferably carried out at a temperature of at least about 500° C., and is most preferably carried out at a temperature in the range of about 500° to about 1200° C.

In a preferred embodiment the reactant gas is air. In another preferred embodiment the reactant gas is a combination of an oxygen-containing gas, preferably selected from air, oxygen-enriched air, nitrogen-enriched air, or substantially pure oxygen, and ammonia. When the reactant gas is a combination of oxygen-containing gas and ammonia, the synthesis reaction is carried out under conditions that effect the substantially complete reaction of the ammonia in the reactant gas.

The nitric oxide synthesis catalyst is preferably a Group VIII noble metal catalyst, preferably a noble metal catalyst, such as platinum, palladium, iridium, rhodium or combinations of these noble metal catalysts. The Group VIII noble metal catalyst can be used in combination with other Group VIII metals, such as nickel, cobalt or iron.

The gas exiting the nitric oxide synthesis reactor is treated to remove any nitrogen dioxide formed during the synthesis reaction. This is preferably accomplished by one or more of water scrubbing, absorption using soda-lime, use of a refrigerated condenser or adsorption using an adsorbent which preferentially adsorbs nitrogen dioxide from the nitric oxide synthesis gas. In the most preferred embodiment, the nitric oxide purification is carried out by adsorption using an adsorbent selected from silica gel, hydrophobic zeolites or mixtures of these.

The purified nitric oxide-containing gas may be blended with air or oxygen to produce a gas mixture of the desired nitric oxide concentration.

BRIEF DESCRIPTION OF THE INVENTION

FIG. 1 illustrates apparatus for carrying out a preferred embodiment of the invention.

Only equipment and lines necessary for an understanding of the invention have been included in the drawing figures.

DETAILED DESCRIPTION OF THE INVENTION

The invention provides a convenient method for providing a stream of air or oxygen-enriched gas containing a therapeutic amount of nitric oxide at the site at which it is to be used. The process can be practiced, for example, in a hospital room or in a patient's home.

The accompanying drawing illustrates a system useful for practice of the process of the invention. The principal equipment units used in the system are a nitric oxide reactor, A and a nitric oxide gas purifier, B.

Reactor A may be any portable reactor vessel suitable for carrying out high temperature chemical reactions. Reactor A is packed with a nobel metal catalyst of the group described above. Reactor A is provided with feed gas inlet line 2 on its inlet side and nitric oxide product gas line 4 on its outlet side. Feed gas line 2 may be connected to a source of air or other suitable oxygen- and nitrogen-containing gas or a gas mixture containing oxygen and ammonia, and optionally nitrogen, e.g. an air-ammonia gas mixture. Alternatively, a source of ammonia gas may be separately provided to the system via line 6. Line 6 may be attached to line 2, as illustrated, or it may be directly connected to reactor A. Heating means is also provided to heat the reactant gas or the catalyst bed to a temperature sufficiently high to effect the desired nitric oxide producing reaction in reactor A. In the drawing, the heating means takes the form of heat exchanger 8, which may be a furnace or other suitable heat exchange means. Alternatively, reactor A can be provided with heating means, such as an electrical resistance or induction heating coil.

Nitric oxide product gas line 4 connects the outlet of reactor A to cooler 10, which serves to cool the product gas to a suitable temperature, which is not critical but is generally in the range of about 0° to about 100° C. The product gas outlet end of cooler 10 is connected to the inlet end of purifier B. Purifier B may be any equipment, preferably portable for purifying a nitric oxide gas stream by removing nitrogen dioxide from the gas stream. Typical appropriate purifiers include water scrubbing devices that wash nitrogen dioxide from the gas stream as dilute nitric acid; absorption units containing, for example, an alkaline substance such as soda lime (a mixture of sodium hydroxide and calcium oxide), which neutralizes nitrogen dioxide from gas streams without affecting the nitric oxide; a refrigerated condenser for solidifying nitrogen dioxide and removing it from the gas stream; and gas adsorption units, which contain an adsorbent substance which more strongly adsorbs nitrogen dioxide than nitrogen oxide.

As noted above, gas adsorption units are most preferred for use in this invention, because of their ability to adsorb nitrogen dioxide using a dry, inexpensive, particulate adsorbent material. These materials are easily adaptable for use in portable units and the adsorbent can be easily replaced when it becomes spent. The adsorbent used in this embodiment can be any substance which more readily adsorbs nitrogen dioxide than nitric oxide. Suitable adsorbents include molecular sieves of the FAU, MFI and MEL type structures, including zeolites that have been made alumina-deficient by dealumination, and molecular sieves that are directly synthesized without introducing alumina groups into the lattice structure. These alumina-deficient molecular sieves include dealuminated type Y zeolite (DAY), ZSM-5, ZSM-11 and ZMS-20, all having silicon to aluminum atomic ratios of at least about 100. Preferred zeolites of this class include aluminum-deficient zeolite 5A, alumina-deficient zeolite 13X, aluminum-deficient zeolite 4A and aluminum-deficient type Y zeolites. Most preferred zeolites are aluminum-deficient type Y zeolite, ZSM-5 zeolite, ZSM-11 zeolite, ZSM-20 zeolite and mixtures of these. Details of such adsorbents and their use in purifying nitric oxide are disclosed in U.S. Pat. No. 5,417,950, the specification of which is incorporated herein by reference.

Adsorbents that are also useful in the invention are metal cation-free adsorbents, including silica gel, alumina, and metal cation-free synthetic zeolites, such as types A, X and Y zeolites, and natural zeolites, such as mordenite, faujasite, chabazite, etc. Preferred adsorbents of this type include silica, alumina and types A, X and Y zeolites. The most preferred adsorbent of this category is silica gel. The terms "metal cation-free" and "substantially free of metal cations" when use in reference to an adsorbent, mean that the adsorbent contains no more than trace amounts of metal cations. These adsorbents and their use in the purification of nitric oxide are disclosed in copending U. S. patent application Ser. No. 271,592, filed Jul. 7, 1994, the specification of which is incorporated herein by reference.

Although the adsorbent in purifier B can be regenerated by subjecting it to pressure reduction or temperature increase, it is generally easier and more cost effective to discard the spent adsorbent and replace it with fresh adsorbent. Since the amount of nitrogen dioxide removed from the nitric oxide is very small, for example usually in the range of about 1 to about 100 ppm, the adsorbent will generally have a useful life of many months.

Water vapor in the product gas stream will generally be adsorbed onto the adsorbents. The nitrogen dioxide reacts with adsorbed water to form nitric acid or nitrous acid, which may destroy the microstructure of the adsorbent and shorten its useful life. Accordingly, it is preferable to remove moisture from the nitric oxide product gas prior to adsorptive removal of nitrogen dioxide therefrom. This can be accomplished by inserting a dryer bed upstream of the nitrogen dioxide adsorbent. Any conventional drying agent, such as alumina, can be used in the dryer bed.

The outlet end of purifier B is connected to a product gas line 12. In the embodiment illustrated in the drawing, oxygen blending line 14 and moisture injection line 16 are connected to line 12.

In the process of the invention as practiced in the system illustrated in the drawing, a feed gas mixture, which may be an oxygen- and nitrogen-containing gas, such as air, or a mixture of ammonia and an oxygen-containing gas, enters the system through line 2. Alternatively, ammonia gas may be separately introduced into the system through line 6. The mixture is passed through heat exchanger 8, wherein it is heated to the desired reaction temperature, for example about 500° C. The heated gas mixture enters reactor A and passes through the bed of catalyst contained in the reactor. As the hot gas mixture contacts the catalyst the ammonia and oxygen react to form a mixture of nitrogen oxides, the mixture being comprised predominantly of nitric oxide and nitrogen dioxide. The temperature in reactor A and the period of time that the reaction gas mixture remains in contact with the catalyst is desirably such that substantially all of the ammonia in the feed is converted to nitrogen oxides. It can be appreciated that the quantity of nitric oxide in the product gas on will depend, to a great extent, upon the amount of ammonia in the gas, and to a lesser extent, on the amount of nitric oxide produced by reaction of nitrogen and oxygen. Under the conditions prevailing in reactor A, ammonia and oxygen react much more readily than nitrogen and oxygen, and since the reaction between ammonia and oxygen is quantitative, the amount of nitrogen oxide in the product gas can be controlled by regulating the concentration of ammonia in the feed gas.

The product gas, comprised predominantly of air, oxygen-enriched air or oxygen, and containing nitric oxide and nitrogen dioxide, leaves reactor A through line 4 and next enters separator B. As noted above, separator B may be a water scrubber, a refrigerated condenser, an absorber or an adsorber. These units are all well known and need not be described in detail. A preferred separator is an adsorber unit, since adsorption avoids the need for liquid handling or complex and expensive equipment. As the product gas passes through separator B substantially all of the moisture and nitrogen dioxide is removed from the gas. If a hydrophobic adsorbent, such as dealuminated type Y zeolite, is used in separator B, moisture will not be substantially removed from the product gas.

The gas exiting separator B, now substantially free of nitrogen dioxide, can be diluted with air or oxygen, if desired. This is accomplished by introducing the air or oxygen into the gas through line 14. Moisture can be introduced into the product gas by means of line 16, which may consist of a water spray or other suitable means. Alternatively, moist air can be introduced into the product gas through line 14, in which case line 16 is unnecessary.

Since oxygen reacts rapidly with nitric oxide to form nitrogen dioxide, it is important that the product gas in line 12 be administered to the patient within a very short time, for example within two seconds or so, after the gas exits separator B. The gas can be administered to the patient using any standard equipment, and such equipment forms no part of this invention.

The apparatus used in the invention can be stationary or portable. In either case the feed gas can be introduced into line 2 from pressurized storage containers, such as gas bottles, or, if air is used as the principal gas vehicle a blower can be use to provide the air at the desired pressure. In the latter case, ammonia can be introduced into the air from a pressurized container. When stationary units are employed large gas containers and elaborate reactor and separator can be used, while portable units are preferably kept as simple and as compact as possible to minimize servicing requirements.

It will be appreciated that it is within the scope of the present invention to utilize conventional equipment to monitor and automatically regulate the flow of gases within the system so that it can be fully automated to run continuously in an efficient manner.

The invention is further illustrated by the following hypothetical example in which, unless otherwise indicated, parts, percentages and ratios are on a volume basis.

A gas mixture comprising 5.39 cc/min of ammonia, 6.74 cc/min of oxygen and 4.52 l/min of nitrogen is passed through a catalytic reactor at ambient pressure and 850° C. The catalyst is a five-layer platinum alloy gauze having a diameter of about 2.5 cm and containing 90% platinum, 5% rhodium and 5% palladium. The product gas issuing from the reactor is cooled to ambient temperature and dried by passage through a condenser and an alumina drying bed. The effluent from the drying bed is passed through a silica gel adsorption bed. The purified gas will contain about 998 ppm nitric oxide and generally less than about 1 ppm nitrogen dioxide.

The above example illustrates the beneficial use of the system of this invention for producing an oxygen-based nitric oxide-containing gas suitable for administration to patients.

Although the invention has been described with particular reference to specific equipment arrangements and to specific experiments, these features are merely exemplary of the invention and variations are contemplated. For example, vertical or horizontal vessels can be used in any of the embodiments of the invention. The scope of the invention is limited only by the breadth of the appended claims.

What is claimed is:

1. A method of producing a continuous stream of nitric oxide-containing inhalant gas suitable for treatment of medical conditions, comprising the steps:

(a) contacting a feed gas comprising oxygen and nitrogen, oxygen and ammonia or oxygen, nitrogen and ammonia with a Group VIII noble metal catalyst which effects the reaction of ammonia and oxygen to form nitric oxide at a temperature in the range of about 300° to about 1200° C., thereby producing a gas mixture containing nitric oxide and nitrogen dioxide;

(b) passing said gas mixture through a bed of adsorbent which preferentially adsorbs nitrogen dioxide, thereby producing a substantially continuous stream of substantially nitrogen dioxide-free nitric oxide-containing product gas.

2. The method of claim 1, wherein said feed gas is air.

3. The method of claim 2, wherein said feed gas comprises air and ammonia and said product gas is substantially free of ammonia.

4. The method of claim 1, further comprising blending said substantially nitrogen dioxide-free product gas with oxygen.

5. The method of claim 1, further comprising introducing moisture into said substantially nitrogen dioxide-free product gas.

6. The method of claim 1, wherein said catalyst is platinum, palladium, iridium, rhodium or mixtures of these.

7. The method of claim 1, wherein said adsorbent is an exchangeable metal cation-free adsorbent selected from silica gel, alumina, zeolites and mixtures of these.

8. The method if claim 7, where said adsorbent is an aluminum-deficient adsorbent selected from dealuminated type Y zeolite, ZSM-5 zeolite, ZSM-11 zeolite, ZSM-20 zeolite and mixtures of these.

9. Apparatus for providing a continuous stream of oxygen-nitric oxide gas mixture to a patient comprising:

(a) a catalytic chamber containing a Group VIII noble metal catalyst which converts a feed mixture comprising oxygen and nitrogen, oxygen and ammonia or oxygen, nitrogen and ammonia to nitric oxide at a reactive temperature in the range of about 300° to about 1200° C., said catalytic chamber having a gas inlet for feed gas and a gas outlet for nitric oxide-containing product gas;

(b) means for heating said feed gas to said reactive temperature;

(c) an adsorption vessel for purifying said nitric oxide-containing product gas by removing nitrogen dioxide therefrom, said adsorption vessel containing an adsorbent which more strongly adsorbs nitrogen dioxide than nitrogen, oxygen and nitric oxide, and having a gas inlet in fluid communication with the gas outlet of said catalytic chamber and a gas outlet for purified nitric oxide-containing product gas;

(d) dispensing means in fluid communication with said gas outlet for purified converted gas for administering purified nitric oxide-containing product gas to a patient; and (e) means for moving gas through said catalytic chamber, said adsorption vessel and said dispensing means.

10. The apparatus of claim 9, wherein said catalyst is platinum, palladium, iridium, rhodium or mixtures of these.

11. The apparatus of claim 9, wherein said adsorbent is an exchangeable metal cation-free adsorbent selected from silica gel, alumina, zeolites and mixtures of these.

12. The apparatus of claim 11, where said adsorbent is an aluminum-deficient adsorbent selected from dealuminated type Y zeolite, ZSM-5 zeolite, ZSM-11 zeolite, ZSM-20 zeolite and mixtures of these.

13. The apparatus of claim 9, further including means for blending oxygen or air with said nitric oxide-containing product gas.

14. The apparatus of claim 9, further including means for introducing moisture into said nitric oxide-containing product gas.

15. The method of claim 1, wherein said nitric oxide-containing product gas contains a substantially constant concentration of nitric oxide.

* * * * *